United States Patent [19]
Ochiai et al.

[11] 3,972,946
[45] Aug. 3, 1976

[54] CATALYST ACTIVITY CONTROL IN PROCESS FOR CONVERTING AN ALKENE TO A CARBONYL DERIVATIVE IN THE PRESENCE OF A NOBLE METAL AND REDOX AGENT

[75] Inventors: Shinya Ochiai; Leonard Griffith, both of Corpus Christi, Tex.

[73] Assignee: Celanese Corporation, New York, N.Y.

[22] Filed: Sept. 22, 1971

[21] Appl. No.: 182,774

[52] U.S. Cl. ........................................ 260/604 AC
[51] Int. Cl.$^2$ ........................................ C07C 45/02
[58] Field of Search ............................ 260/604 AC

[56] References Cited
UNITED STATES PATENTS

| | | | |
|---|---|---|---|
| 3,076,032 | 1/1963 | Riemenschneider et al. | 260/604 AC |
| 3,119,875 | 1/1964 | Steinmetz et al. | 260/604 AC |
| 3,154,586 | 10/1964 | Bander et al. | 260/604 AC |
| 3,346,626 | 10/1967 | Schaeffer et al. | 260/604 AC |

OTHER PUBLICATIONS

"Chemistry and Industry" Jan. 13, 1962 Dr. J. Smidt pp. 54–61.

*Primary Examiner*—James O. Thomas, Jr.
*Assistant Examiner*—A. Siegel
*Attorney, Agent, or Firm*—Ralph M. Pritchett

[57] ABSTRACT

In converting an alkene such as ethylene to a carbonyl derivative such as acetaldehyde by a process which comprises passing the alkene through a tubular reactor along with an aqueous acidic catalyst solution comprising a noble metal such as palladium together with a cupric chloride redox agent, followed by separating the carbonyl product from the depleted catalyst solution which is then reoxidized with a source of molecular oxygen such as air prior to being returned to the reactor, continuous depletion of the chloride content of the catalyst solution takes place as a result of the formation of chlorinated reaction by-products. This necessitates replenishment of the chloride content of the catalyst solution by adding hydrochloric acid into a catalyst regeneration zone preceding the catalyst reoxidation step of the process. Over-treating or under-treating with the hydrochloric acid results, however, in occasional process upsets and failure to maintain optimal activity of the catalyst solution and maximum reactor output. The present invention comprises maintaining optimal catalyst activity by adding hydrochloric acid in response to the hydraulic pressure gradient obtaining within the alkene-oxidation reactor, within which a deficiency of acid causes an increasing hydraulic pressure gradient due to fouling of the tubular reactor with precipitated solids. Optimal catalyst activity obtains when the acid addition rate is just sufficient to prevent the inception of a pressure gradient rise due to precipitation of solids within the reactor.

10 Claims, 2 Drawing Figures

CATALYST ACTIVITY CONTROL IN PROCESS FOR CONVERTING AN ALKENE TO A CARBONYL DERIVATIVE IN THE PRESENCE OF A NOBLE METAL AND REDOX AGENT

BACKGROUND OF THE INVENTION

This invention relates to the conversion of alkenes, especially lower alkenes and specifically ethylene, to carbonyl derivatives such as acetaldehyde (when the alkene is ethylene) and ketones (when the alkene is propylene or a higher alkene) by a two-stage process in which the alkene is reacted (in the first stage of the process) with an aqueous acidic solution of an oxidant catalyst system comprising a noble metal (especially palladium) together with a redox agent comprising cupric chloride, the carbonyl compound then being separated from the spent catalyst solution which is then (in the second stage of the process) reoxidized with a source of molecular oxygen (typically air) before being recycled to the first stage of the process for the conversion of additional quantities of the alkene.

Although the conversion of ethylene to acetaldehyde is presently the most important variant of the process commercially, it can also be employed to convert other alkenes, particularly lower alkenes and more particularly alkenes having up to about six carbon atoms, to corresponding ketone derivatives. For example, propylene can be converted to acetone and 1-butene and 2-butene can be converted to methyl ethyl ketone.

The process is described, for example, in a paper by Dr. J. Smidt in "Chemistry and Industry" (Jan. 13, 1962), pages 54–61. This paper describes both the two-stage process, with which the present invention is concerned, and a closely-related single-stage process, which does not employ a separate catalyst reoxidation step and which is less closely related to the present invention.

The details of the reaction mechanisms are not pertinent to the present invention, with one exception: this is that the formation of chlorinated by-products, which are continuously withdrawn from the reaction product mixture in the course of product recovery in purification, results in a continuous depletion of the chloride content of the catalyst solution, which in turn results in reduced catalyst activity (i.e. reduced productivity per unit volume of the alkene-oxidation reactor), necessitating replenishment of the chloride content of the catalyst solution by adding hydrochloric acid. This makeup acid, in aqueous solution, is customarily admixed with a slip stream drawn from the main stream of oxidized catalyst solution leaving the catalyst reoxidation stage of the process and being forwarded to the alkene-oxidation stage. This slip stream, admixed with the makeup hydrochloric acid, is passed through a "catalyst regeneration" zone in which, in addition to incorporating the fresh acid into the solution, the heated mixture of catalyst solution and hydrochloric acid is also allowed to react at elevated temperature (e.g. about 160°C) to decompose certain undesirable organic byproducts including oxalates. The process can, if desired, be operated without a separate catalyst regeneration zone, in which case the makeup hydrochloric acid is simply incorporated into the depleted catalyst solution entering the catalyst reoxidation stage of the process.

It is known that the composition of the catalyst solution should be controlled within certain limits for optimal chemical efficiency, but heretofore it has been necessary as a practical matter to allow more fluctuation in its composition than is desired. More particularly, the nature of the catalyst solution is such that it does not readily lend itself to rapid "on-line" chemical analyses from which fine adjustment of its composition can be readily and quickly carried out in the production plant. On-line analysers for either chloride or copper ion in this solution are not available. Because of this, the ordinary mode of operation has heretofore entailed periodic conventional chemical analysis followed by a rather extended adjustment of the hydrochloric acid flow on what amounts to a trial and error basis in an effort to compensate for the continuing loss of chloride moiety from the system and maintain a constant catalyst composition.

The method of hydrochloric acid flow adjustment just described has two deficiencies. First, to the extent that it results in under-treatment, it results in under-utilization of the alkene-oxidation reactor. Such under-utilization, by which is meant in the present context operation at roughly 90% or less of maximum reactor capacity, is more than ordinarily important in this particular process, since the highly corrosive nature of the catalyst solution requires use of process equipment which is fabricated of, or lined with, titanium, so that, more than in many other chemical processes, under-utilization of the reaction apparatus is a substantial economic drawback. Second, over-treatment, as distinguished from under-treatment, has consequences which are also unacceptable. Specifically, over-treatment also results in a lowering of catalytic activity to such an extent as to cause a rapid "upset" in the reaction with a sudden decrease in conversion and resulting rise in the amount of alkene which passes through the reactor unconverted.

Heretofore, plant operation of the alkene oxidation process has been characterized by periodic "upsets" caused by operating with either too much or too little hydrochloric acid, such that, even with the most conscientious attention, the productivity of the reaction system falls short of its maximum capability by an amount which is of the order of 10% or more.

It is an object of the present invention to provide an improved process control system by means of which the reactor productivity can be easily maintained at its optimal level in processes of the sort described wherein an alkene is oxidized to a carbonyl derivative with an aqueous solution of a noble metal, particularly palladium, and a redox agent, particularly copper chloride, in a two-stage system of tubular reactors the first of which is an alkene-oxidation reactor while the second is a catalyst solution reoxidation reactor in which the components of the catalyst solution are reoxidized with a source of molecular oxygen, such as air.

It is a specific object to provide a reliable and effective method for controlling the rate of addition of hydrochloric acid into a catalyst regeneration zone operated in conjunction with the catalyst reoxidation system contained in a two-stage process, as described above, for oxidizing a lower alkene such as ethylene to a carbonyl derivative such as acetaldehyde.

Other objects will be apparent from the following detailed description, example, and claims.

SUMMARY OF THE INVENTION

The present invention is based on the discovery that optimal catalyst solution activity and alkene oxidation reactor productivity obtain when the hydrochloric acid content of the catalyst solution is at such a level that any decrease in acid concentration will result in precipitation of cuprous chloride, and that the cuprous chloride precipitation resulting from under-treatment with acid results in an increase in pressure gradient through the alkene oxidation reactor (i.e. it results in an increase in hydraulic pressure drop due to fouling of the tubular reactor with precipitated solids) which is of such magnitude that it can be sensed by suitable pressure-sensing instruments so that variations in reactor pressure gradients can be employed as process control inputs from which the hydrochloric acid injection rate is controlled by conventional flow-control means. That is, the hydrochloric acid addition is controlled directly in response to the reactor pressure gradient at such a rate as to maintain the catalyst solution at or very near the point of incipient solids precipitation. By this method the composition of the catalyst solution can be controlled closely over long periods of time without the need for frequent analyses of the solution.

In a preferred embodiment of the invention, which is particularly useful when ethylene is being oxidized to acetaldehyde, the rate of discharge of unreacted alkene in the fixed gases vented from the product recovery system of the process is also monitored (by continuously metering the vent gas flow rate while also monitoring its alkene concentration with a conventional on-line analyzer), and the rate of discharge of unreacted alkene (the alkene vent rate) is also employed as a process control input along with the reactor pressure gradient already discussed. The alkene vent rate, it has been discovered, increases when the hydrochloric acid addition rate is too high, just as the reactor pressure gradient increases when the acid addition rate is too low, so that optimal reactor productivity obtains when the hydrochloric acid addition rate is controlled between a lower limit signaled by an increase in reactor pressure gradient and an upper limit signaled by an increase in the alkene vent rate obtaining at a given throughput rate of catalyst solution and alkene through the alkene oxidation reactor. It will be recognized that, although it is especially applicable to oxidizing ethylene to acetaldehyde, this embodiment of the invention is also readily applicable in oxidizing other lower alkenes which are of sufficient volatility that they can be discharged from the product recovery in a gaseous stream which is easily metered and continuously analyzed by conventional analyzers. For example, propylene and the butylenes have sufficient volatility in this regard.

Although the invention is most readily understood in connection with operation of the alkene oxidation reactor at fixed catalyst solution and alkene throughput rates, it can also be applied under conditions where these rates vary, as will be explained.

DETAILED DESCRIPTION OF THE INVENTION AND PREFERRED EMBODIMENTS

Figure 1:
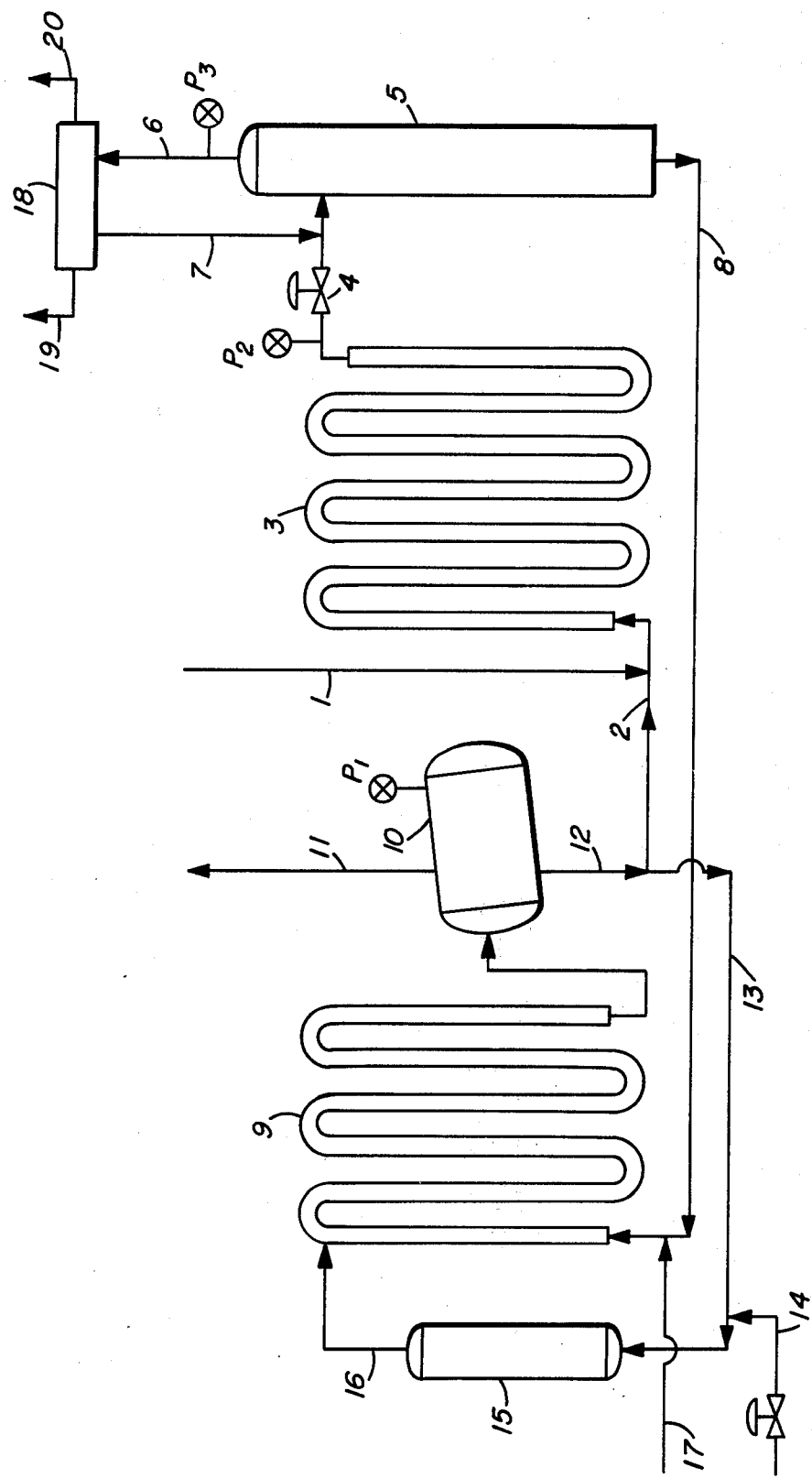

The two-stage alkene oxidation process in which the invention is applied is shown schematically in the drawing, FIG. 1. In the following description ethylene will be employed as the alkene being processed, with acetaldehyde being the reaction product, but as previously explained it will be understood that other alkenes, especially lower alkenes having up to, for example, about 6 carbon atoms are also oxidized to produce corresponding ketone derivatives.

An oxidant catalyst solution comprising an aqueous solution of palladous chloride, cupric chloride, and hydrochloric acid, which is drawn from separator 10 through conduit 2, is mixed with ethylene introduced through conduit 1 and the resulting mixture is passed through alkene-oxidation reactor 3 at a temperature of about 110°C and under a pressure of about 11 atmospheres absolute. The catalyst solution comprises approximately 6 millimoles per liter of palladous chloride, 1000 millimoles per liter of cupric chloride, 100 millimoles per liter of cuprous chloride, 8 weight percent of acetic acid, and the remainder water. Small quantities of organic reaction by-products may also be present to the extent that these have passed through the product recovery and catalyst regeneration systems which will be described.

In the alkene oxidation reactor the ethylene is oxidized to acetaldehyde at nearly 100% conversion per pass, while simultaneously at least a portion of the cupric chloride, which acts as a redox agent in conjunction with the palladous chloride catalyst, is chemically reduced to cuprous chloride. Thus the product discharged from the alkene oxidation reactor is an aqueous solution containing hydrochloric acid, copper chlorides, and palladium moiety which may be present as the chloride, as $Pd°$, or as a mixture of the two. Also present will be a quantity of gases comprising any unreacted ethylene as well as any fixed gases which are formed in the reaction. Also present are small quantities of dissolved reaction by-products such as chloroacetaldehydes, oxalate ions, etc.

The reaction product just described is discharged through throttle valve 4, which acts to maintain a constant back-pressure at a point at or near the discharge end of the reactor. Throttle valve 4 discharges into stripping tower 5, in which acetaldehyde and other volatile reaction products are stripped from the catalyst solution along with any fixed gases, such as ethylene, which are present.

The stripped-out volatile materials pass from the stripping tower through conduit 6 into product recovery and purification system 18, which is shown in the drawing as a simple rectangle for the sake of simplicity although it will be recognized that this in actual fact is a complicated system of distillation towers etc. in which the crude product mixture is separated into acetaldehyde product (withdrawn through conduit 20), a vent gas stream (discharged through conduit 19), and recycled water (returned to the stripping tower through conduit 7 along with such fresh water as may be needed to maintain a constant inventory of water in the reaction system). It will be recognized also that volatile reaction by-products, e.g. chlorinated organic compounds, also enter the product recovery system through conduit 6 and are ultimately separated from the acetaldehyde and disposed of.

As regards the present invention, details of the product recovery system are not relevant except that (a) fixed gases including ethylene are ultimately discharged, as through conduit 19, in such a manner that their rate of production can be metered and their ethylene content continuously analyzed, and (b) the inventory of catalyst solution within the reaction system is maintained substantially constant by returning water from the product recovery system through conduit 7 and/or by adding fresh water to the system at such a rate as to compensate for water withdrawn from the stripping tower through conduit 6.

Stripping tower 5 acts, as has been explained, to remove volatile and gaseous materials from the reactor product discharged from reactor 3. It operates at a constant pressure of approximately 1.5 atmospheres absolute when the process is being employed to convert ethylene to acetaldehyde. The stripped catalyst solution drawn from the base of the stripping tower through conduit 8 comprises an aqueous solution of hydrochloric acid, palladium moiety, cupric and cuprous chlorides, and non-volatile reaction by-products such as oxalates and non-volatile chlorinated organic compounds. This chemically reduced depleted catalyst solution is mixed with air or other equivalent source of molecular oxygen and passed through catalyst reoxidation reactor 9, within which cuprous chloride contained in the catalyst solution is reoxidized to the cupric form in the course of being cocurrently through the reactor 9 with the oxygen. Reactor 9 operates at approximately 12 atmospheres absolute and at a temperature of approximately 115°C, with sufficient oxygen being present to oxidize all the introduced cuprous salts to the cupric form.

The reoxidized catalyst solution discharged from reactor 9 enters gas-liquid separator (oxygen separator) 10, which is typically operated at a constant pressure of approximately 11 atmospheres absolute. Excess oxygen and any inert gases, e.g. nitrogen, which are present are discharged from separator 10 through conduit 11, while the reoxidized catalyst solution, now freed from gases, is drawn off through conduit 12.

The solution drawn from the separator through conduit 12 is split into a main stream, which is returned to the alkene-oxidation reactor through conduit 2, and a slip stream which is diverted to catalyst regeneration reactor 15 through conduit 13, along with hydrochloric acid which is introduced at a controlled rate through conduit 14.

Details of the operation of the regenerator 15 are outside the scope of the present invention, except that it operates at approximately 160°C and 13 atmospheres absolute to decompose acid-decomposable reaction by-products including specifically oxalate moiety and to reincorporate sufficient hydrochloric acid into the catalyst solution to compensate for the chloride moiety withdrawn from the system through conduit 6 in the volatile reaction products stripped out of the alkene-oxidation reactor product. Acid-treated catalyst solution discharged from the regeneration reactor is returned to the reoxidation reactor 9 through conduit 16.

Both reoxidation reactor 9 and alkene-oxidation reactor 3 are elongated tubular reactors, each being composed of a series of vertically-oriented tubes connected with U-bends to form an elongated reaction path for the mixture of liquid and gas passing cocurrently therethrough. Typical liquid throughput in each of these reactors is of the order of 9 cubic feet per second per square foot of tube cross-section. Because of the extremely corrosive nature of the catalyst solution, the reactors, as well as other process apparatus exposed to the catalyst solution, are either fabricated of titanium or lined with titanium.

In operation of the system just described, constant pressures are maintained in separator 10, at the discharge end of reactor 3, and in stripping column 5. These pressures are indicated by the symbols $P_1$, $P_2$, and $P_3$, respectively, on the drawing adjacent to symbols which are intended to indicate pressure-sensing, or preferably pressure-sensing and transmitting, instruments. The flow of liquids and gases through reactors 9 and 3 is also maintained at as constant a rate as is possible, and, as has been noted previously, the volume of catalyst solution within the over-all system is also maintained constant by replenishing water losses from the system through, for example, conduit 7.

The present invention is based primarily upon controlling the rate of introduction of hydrochloric acid through conduit 14 on the basis of observed fluctuations in the pressure gradient obtaining through the alkene-oxidation reactor 3 as measured by changes in the observed difference between $P_1$ and $P_2$. In a more preferred embodiment the rate of acid addition is, in addition, controlled in part by observed variations in the rate of discharge of alkene-containing vent gases through conduit 19. In a particularly useful embodiment of the invention the rate of acid addition is controlled, even though the rate of throughput of catalyst solution through reactor 3 varies, by incoporating into the control scheme a solution flow rate compensation which is made by considering the difference between $P_2$ and $P_3$ in conjunction with the observed degree of opening of throttle valve 4.

The basis of the invention lies in the observation that maximal catalyst activity and reactor productivity in the alkene-oxidation reactor obtain when the hydrochloric acid content of the catalyst solution is adjusted as closely as possible to that level below which incipient precipitation of solids (i.e. cuprous chloride) obtains in the alkene-oxidation reactor and that, in such a reactor operating at or near its maximum output level, such precipitation of solids causes an increase in pressure gradient through the reactor (i.e. an increase in hydraulic pressure drop due to fouling of the reactor internals with solids) which is of such magnitude that the increase in pressure gradient can be detected by suitable instrumentation and employed as a process control input for suitable flow-control apparatus controlling the rate of hydrochloric acid injection into the catalyst regenerator to maintain the acid introduction rate above that level at which solids precipitation occurs. It has also been discovered that, with the lower limit of acid introduction being controlled by the reactor pressure gradient just discussed, an upper limit for the acid introduction rate can also be set on the basis of the rate of discharge of unreacted alkene through conduit 19 at a given rate of alkene throughput through reactor 3. More specifically, an undesirable excess of hydrochloric acid addition is signalled by the inception of a rising trend in the alkene vent rate. Thus it becomes possible to control the hydrochloric acid addition rate at an optimal level by utilizing the simple physical parameters of alkene-oxidation reactor pressure gradient and alkene vent rate without the necessity of frequently carrying out chemical analyses of the catalyst solution followed by stoichiometric calculations and subsequent periodic readjustments of the acid flow rate with attendant loss of time and risk of upsets in reactor operation while these adjustments are being carried out.

In semi-quantitative terms, it has been discovered that employment of the present process control method, as compared with the previous method of periodically analyzing the catalyst solution and readjusting it on the basis of the analytical results, allows an increase of alkene-oxidation reactor productivity of the order of about 10% as well as simplifying the work of the plant operating staff and avoiding periodic upsets in reactor operation.

The foregoing explanation of the basic principles of the invention implicitly assumes that the reactor pressure gradient and the alkene vent rate are measured at constant conditions of alkene and catalyst solution throughput through the reactor. It is not essential, however, that these flow rates be maintained at absolutely unvarying levels, because it has also been discovered that variations in reactor throughput rate can be compensated for by utilizing changes in the degree of opening of throttle valve 4 as it adjusts itself under conditions of varying throughput to maintain a constant back-pressure within the alkene-oxidation reactor while discharging into the constant-pressure environment of stripping column 5. This mode of operation is based on the concept of a catalyst solution flow rate-compensated reactor pressure gradient M, variations in which can be expressed by the following equation:

$$\Delta M = C_1 [\Delta(P_1-P_2)-C_2\Delta F_R)], \qquad (I)$$

wherein $M$ is the reactor pressure gradient compensated for variation in catalyst solution throughput rate, $(P_1-P_2)$ is the reactor pressure gradient as actually measured, $F_R$ is the rate of solution throughput through the reactor, $C_1$ and $C_2$ are positive constants, and the notation $\Delta$ signifies a change in the indicated term.

Equation I as just set forth is valid especially under conditions of minor deviation from unfouled-reactor operating conditions, which are the conditions at or near which operation of the alkene-oxidation reactor is maintained in the present control method. In this equation the term $F_R$ relates directly to the position, i.e. the degree of opening, of throttle valve 4, since the degree of opening of this valve is a direct function of the reactor discharge rate. Thus the output of any suitable transmitting instrument which senses the degree of opening of the throttle valve is a direct indication of the rate of discharge of reaction product from the alkene-oxidation reactor, and for control purposes the actual volumetric flow rate need not be known. This is especially useful since, solids sometimes being present, it is very difficult to meter the actual flow rate of the reactor product at all times with conventional instruments. It will be seen, therefore, that adding hydrochloric acid to the catalyst regenerator at such a rate as to maintain $\Delta M$ at 0 in Equation I results in the desired maintenance of a hydrochloric acid concentration which is high enough to avoid precipitation of solids in the alkene-oxidation reactor and that this can be accomplished even though the alkene-oxidation reactor throughput varies from a constant value.

Just as term $F_R$ in Equation I above need not be known directly, i.e. the position of the throttle valve as sensed, and preferably sensed and transmitted, by some suitable instrument can be employed as the control parameter without actually knowing the actual volumetric flow rate, so is it unnecessary that $P_1$ and $P_2$ be known directly. That is, all that is required in an automatic control scheme is that the outputs of suitable instruments sensing pressures $P_1$ and $P_2$ be available as inputs for conventional control instrumentation. These outputs, like the output of the instrument sensing the degree of opening of the throttle valve discussed above, can be, for example, the pneumatic outputs of pneumatic indicators or controllers, or they may be electrical outputs, e.g. voltages, emitted by suitable electrical or electronic instruments, preferably transmitting instruments. Even simple mechanical linkages can be employed, although electrical or pneumatic transmitting instruments are preferred.

The foregoing has dealt with means for handling the reactor pressures and reactor product discharge rate dealt with in Equation I, which describes the conditions to be controlled having to do with the pressure gradients in the alkene-oxidation reactor, which in turn relates, as has been explained, to the lower control limit of hydrochloric acid introduction rate into the process. The following relates to control of the upper limit of hydrochloric acid introduction rate, which is related not to reactor pressure gradient but rather to the rate of discharge of unreacted alkene from the product recovery section of the process through a suitable discharge line, e.g. conduit 19 in the drawing, through which the rate of flow of the vent gases can be continuously metered by any suitable means, such as an indicating, and more preferably a transmitting, flowmeter while alkene content is also monitored by an on-line analyzer.

As has been explained, the optimal level of hydrochloric acid concentration in the catalyst solution is that at which any further decrease in hydrochloric acid concentration will result in solids precipitation in the alkene oxidation reactor (which is signalled by an increased pressure gradient). When the hydrochloric acid content of the solution becomes higher than this optimal level, there is, of course, no change in reactor pressure gradient, and so this parameter is of no value in signalling an undesirably high acid concentration. It has been observed, however, that when the acid concentration rises above this optimal level, the conversion of alkene within the alkene oxidation reactor declines, with the result that, at a given rate of alkene and catalyst solution throughput through the reactor, undesirably high hydrochloric acid concentration manifests itself in a noticeable increase in the alkene vent rate caused by the appearance of increased quantities of unreacted alkene in the reactor product. It thus becomes possible to adjust the hydrochloric acid introduction rate between a lower limit signalled by an increase in reactor pressure gradient and an upper limit signalled by an increase in the alkene vent rate and automatic instrumentation can be employed to control the acid introduction rate in response to two process signals: (a) the alkene vent rate and (b) the reactor pressure gradient (which may be compensated for variations in catalyst throughput rate as previously explained). With further reference to the alkene vent rate, the alkene oxidation reactor is normally operated with an alkene throughput such that, with the hydrochloric acid concentration at that level at which conditions of incipient solids precipitation obtain, a barely detectable concentration of alkene is observed in the vent gas. It is possible, of course, to operate under conditions such that essentially no alkene at all can be detected in the vent gas, but under these conditions it will be understood that the reactor is not operating at its maximum capacity. Ordinarily, the reactor is preferably operated with an alkene throughput rate such that the vent gas contains roughly 5 to 15 % alkene (e.g. ethylene) by volume. By observing the volumetric flow rate of the vent gas and its alkene content under these conditions, a desirable base alkene vent rate typical of satisfactory operation is obtained, and subsequent increases in the rate above this base rate can be employed, for control purposes in practicing the present invention, as indications that the desired upper limit of hydrochloric acid introduction rate has been attained or exceeded. It is to be understood that some moderate increase in alkene vent rate above that prevailing at optimal conditions does not indicate that the reactor has suddenly become inoperative; i.e. the vent rate can be allowed to increase by a moderate amount above that obtaining at optimal conditions without the occurrence of a serious process upset, but it is recommended that, within the sensitivity of the instrumentation available, such vent rate increases be prevented as much as possible. In any event it is particularly recommended that the alkene vent rate be controlled below that rate at which the alkene contained in the vent gas stream amounts to as much as 0.5% of the alkene introduced into the alkene oxidation reactor.

In the foregoing discussion of alkene vent rate as a factor in controlling the hydrochloric acid addition rate, it will be recognized that when higher alkenes, e.g. pentenes and hexenes, are being oxidized to their carbonyl derivatives, part or all of the alkene which passes through the alkene oxidation reactor unconverted, to be subsequently forwarded to the product recovery system 18 by way of conduit 6 in the drawing, will be liquid rather than vapor at ordinary temperatures and pressures and therefore will ultimately be discharged from the product recovery system as a stream of liquid alkene rather than as vent gas. While it is easier to sense small fluctuations in flow rate of a material in vapor form as compared with liquid form (volumetric flow rate of the vapor being much greater), it will be understood that in the present context the flow rate of a liquid alkene discharged from the product recovery system can be continuously monitored and employed in the present control method just as vent gas flow rate is monitored and used as a control factor when a normally gaseous alkene, e.g. ethylene, is being oxidized.

The following procedures are recommended for establishing the basic process pressures and flow rates which are controlled in the employment of the present method:

First, regarding temperatures, pressures, alkene oxidation reactor space velocity, and basic catalyst composition, these are as already known in the art as it relates to the catalytic alkene oxidation process and, although they have been discussed briefly hereinabove, their optimal values are outside the scope of the present invention, which relates only to a control technique whereby the optimal hydrochloric acid introduction rate is maintained.

Considering now the determination of the "clean" or "unfouled" reactor pressure gradient which is to determine the lower control limit of hydrochloric acid introduction rate, the recommended first step is to determine the pressure gradient obtaining within the alkene oxidation reactor when it is known to be free of internal solids deposits and while the throughputs of catalyst solution and alkene are at the levels it is desired to maintain. This can be accomplished by, first, bringing the alkene oxidation reactor into operation under conditions of temperature, pressure, catalyst solution composition, and throughput of catalyst solution and alkene which are substantially at the levels of these several parameters customarily employed for the process and then subsequently adjusting them if necessary as follows:

First, with the catalyst solution reoxidation reactor also in operation and with a slip stream being drawn from the oxygen separator and passed through the catalyst regeneration reactor at a convenient rate, e.g. about 1% of the solution drawn from the oxygen separator, hydrochloric acid introduction into the slip stream entering the regeneration reactor is initiated at a rate determined by experience to be somewhat less than that which is typically required to compensate for loss of volatile chlorides in the product recovery section of the process.

With hydrochloric acid being introduced as above, operation of the system is continued while the alkene oxidation reactor pressure gradient, i.e. the pressure difference between points $P_1$ and $P_2$ shown on the drawing, is continuously observed. The initial pressure gradient so observed is noted as the reactor pressure gradient obtaining under "clean reactor" conditions at the rate of flow of catalyst solution and alkene feedstock initially employed. The rate of hydrochloric acid introduction obtaining at this time is also noted as a base hydrochloric acid addition rate, which is subsequently to be readjusted as required.

Operation is continued in this manner until an increase in the reactor pressure gradient is observed; in typical plant conditions, a pressure gradient increase of about 0.5 lb per square inch can be reliably detected out of a total reactor pressure gradient, measured between points $P_1$ and $P_2$, of approximately 10 lb per square inch in an alkene oxidation reactor approximately 600 feet long.

In the event the initially selected hydrochloric acid addition rate is too high for an increase in reactor pressure gradient to be manifested, the base rate of hydrochloric acid addition is reduced in stepwise increments until a base rate is obtained at which, after about 5 or 6 hours of reactor operation, an increase in pressure gradient does occur.

After an increase in reactor pressure gradient has been observed, the rate of hydrochloric acid addition to the catalyst regeneration reactor is increased by successive increments, of the order of 10% or less, until a hydrochloric acid introduction rate is reached at which a downward trend in the pressure gradient is observed. This acid addition rate is then maintained until no further decrease in pressure gradient is observed, indicating that the internal surfaces of the reactor are free of solid deposits.

The above sequence of operations is repeated, i.e. lowering the hydrochloric acid rate until the pressure gradient begins to increase followed by increasing the acid rate again until the pressure gradient again indicates a clean reactor, successive adjustments of the hydrochloric acid rate being made within progressively narrower upper and lower limits until, by this trial-and-error procedure, the hydrochloric acid rate is arrived at which is just sufficient to prevent the onset of an increase in the pressure gradient.

With the hydrochloric acid rate and the solution throughput rate being as finally arrived at by the above procedure, the alkene introduction rate is then adjusted, if necessary, until a small quantity of residual unreacted alkene, but only a small quantity, can be detected in the process vent stream by conventional chemical or physical analysis. Typical good operating conditions obtain when the vent stream contains approximately 5% alkene (.e.g ethylene) by volume.

With operating conditions set as above, the base rates for all the flow rates around the alkene oxidation reactor system and the catalyst regenerator system are then noted, and the reactor pressure gradient and, preferably, the position of the throttle valve 4, are also noted as well as the rate of introduction of hydrochloric acid into the catalyst regenerator. For maximal alkene oxidation reactor output, all of the system flow rates can then be further adjusted, in direct proportion to one another, until a condition is reached at which, even though acid introduction rate is correct as determined by readjustment in accordance with changes in reactor pressure gradient as described above, the alkene content of the vent stream nevertheless begins to increase, indicating that total reactor throughput has reached a level at which the available reactor volume is insufficient. All the process flows and pressures obtaining just before this indication of the attainment of maximum reactor capacity is observed are noted as adjusted, maximal base values to be employed in subsequent control of the process at maximum productivity.

At this point, i.e. with all pertinent process flows and pressures at the desired level, including operation of stripping column 5 at its customary normal operating pressure, the constants appearing in Equation I can be determined. It will be recognized, of course, that knowledge of the actual numerical values of the constants is not required for practice of the invention in its broader aspects although the information is useful. It is particularly useful to have values for the constants for use in controlling the process under conditions in which the rate of catalyst solution throughput through the alkene oxidation reactor varies with the result that it is needed to employ, in the process control scheme, a reactor pressure gradient which is compensated for variation in the reactor throughput rate. Values of the constants are determined by varying the catalyst solution flow rate from its base level for a short period of time, e.g. for 1 or 2 minutes, by an amount of, for example, 15% or so above or below the base flow rate and observing $P_1$, $P_2$, $P_3$, and the position of throttle valve 4 obtaining during each condition of changed reactor throughput rate. This provides adequate numerical information for computation of the constants, in which any system of internally consistent units can be employed. For example, actual pressures and actual open area in the throttle valve throat can be employed if desired, or actual pressures in conjunction with the amount of linear movement of the throttle valve stem can be employed. It is also possible and convenient, since in the last analysis the only purpose is to prevent variation from a desired target value of reactor pressure gradient, to determine a set of constants expressed simply in terms of, for example, output signal levels from transmitting instruments sensing the three pressures and the position of the throttle valve.

The vent gas discharge rate, e.g. through conduit 19 shown in the drawing, is important in process control but is not related to determination of the constants $C_1$ and $C_2$ except that when the constants are determined the vent gas rate should be at about the level expected to characterize normal good operation of the reactor. That is, when the constants are determined the vent gas rate should not be so high that reactor pressure gradient and degree of throttle valve opening are unduly influenced by the flow of an abnormally high amount of gas through the system.

With the basic flow and pressure data in hand as determined above, the process can be operated either with minimal instrumentation or else with a high degree of automation. Operation with minimal instrumentation simply entails, preferably, operation with a constant catalyst solution throughput through the alkene oxidation reactor while controlling the hydrochloric acid introduction rate, in response to observed values of reactor pressure gradient and alkene vent rate, between a lower limit the attainment of which is signalled by an increase in reactor pressure gradient and an upper limit the attainment of which is signalled by a perceptible rise in alkene vent rate. Hand control of the flow rates can be employed in this manner, if desired, in conjunction with simple instrumentation for monitoring the process pressures $P_1$ and $P_2$ and for controlling pressure $P_3$ at a constant value.

Application of the invention under conditions when the catalyst solution throughput rate does not remain constant is better understood by considering the degree of reactor fouling as being represented by an index I which is expressed mathematically in the following equation:

$$\Delta I = a\Delta X - b\Delta Y \qquad (II)$$
$$= a\Delta(P_1-P_2) - b\Delta[(P_2-P_3)_V]$$

in which $X$ is the alkene oxidation reactor pressure gradient, $Y$ is the catalyst solution throughput rate, $P_1$, $P_2$, $P_3$ are system pressures as shown on the drawing, $a$ and $b$ are positive constants, the subscript $V$ indicates conditions obtaining at a given position of the reactor outlet throttle valve, and $\Delta$ represents an increment in the indicated term.

Figure 2:
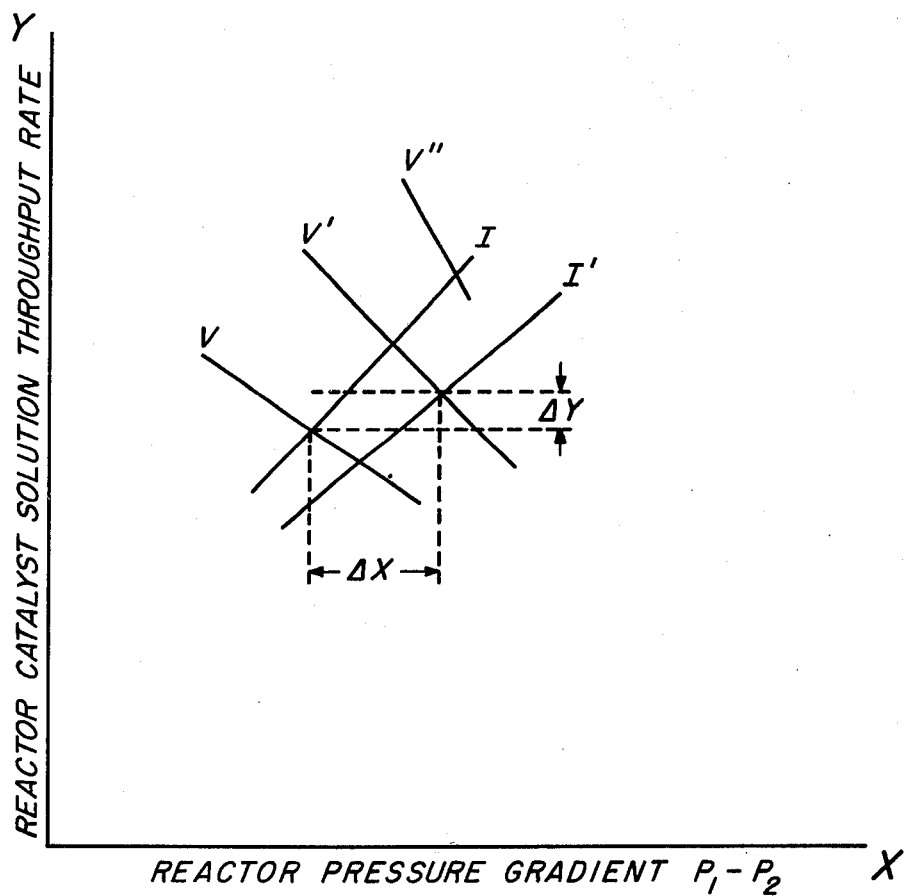

The significance of this index I and its relation to the other terms in Equation II (which equation can be seen to be related to Equation I) is shown in FIG. 2, in which the lines marked V and V' designate conditions obtaining at two different positions of the throttle valve while the lines designated I and I' designate conditions obtaining at two different degrees of reactor fouling (e.g. line I may indicate conditions obtaining when the reactor is free of solid deposits while I' would indicate conditions obtaining when there are solid deposits within the reactor resulting in an increase in reactor pressure gradient). The lines as shown in FIG. 2 are straight and therefore apply to a very small incremental change in the parameters being discussed; it will be recognized that changes in, for example, catalyst solution throughput, over a wide range would result in curved lines in FIG. 2.

Considering operation at constant catalyst solution and alkene throughput rates and with a clean, i.e. unfouled, reactor, and also assuming that $P_3$ remains at a constant value as is normally the case, the throttle valve will remain in one position and a given rate of catalyst throughput will be associated with one uniquely determined reactor pressure gradient. This condition is represented by the intersection of the lines marked V and I on the graph. Assuming now that the solution throughput is increased but that the internal surfaces of the reactor remain clean, the throttle valve will open, and conditions will be as represented by the intersection of the lines marked I and V'. Increasing the catalyst throughput to an even higher rate, while the reactor remains in an unfouled condition, would result in a condition which is represented by the intersection of line I and line V'' (line V'' representing a third position of the throttle valve). It can be seen that in this manner it is possible, if desired, to plot a graph relating the degree of opening of the throttle valve to the rate of catalyst solution throughput through the unfouled alkene oxidation reactor.

Considering now conditions obtaining when solids have been deposited in the reactor with resulting increase in pressure gradient, such a condition is indicated on the graph by the lower of the two horizontal dotted lines, which shows that, at a constant catalyst solution throughput rate, fouling of the reactor shifts the index to a point represented on the graph by the intersection of line I' and the lower horizontal dotted line. The throttle valve would also open to a position intermediate between V and V'.

Assuming now a condition in which reactor fouling has taken place together with an increase in reactor catalyst solution throughput rate, conditions are as shown in FIG. 2 as follows:

Operation under conditions of the new fouling index is shown by line I'. The increase in catalyst throughput rate is shown by the increment $\Delta Y$, and the increase in reactor pressure gradient is shown by $\Delta X$. It will be seen that, had there been an increase in solution throughput rate without any reactor fouling, conditions would have been as indicated in FIG. 2 by the intersection of the upper horizontal dotted line and line I; any shift of operating conditions into the area which is to the right of line I on FIG. 2 indicates reactor fouling and, in the present context, the need to increase hydrochloric acid introduction rate to restore flow-pressure gradient-valve position conditions to those represented by line I. It can be seen that the exact delineation of fouled conditions represented by, for example, line I', is not necessary although it is helpful in indicating the degree to which hydrochloric acid introduction rate should be increased on a short-term basis; all that is essential is to know that conditions have shifted somewhere to the right of line I.

It will be seen that it is possible to design process control apparatus, e.g. electronic instrumentation, to sense catalyst solution throughput rate, reactor pressure gradient, and throttle valve position and to control, on the basis of these inputs, the addition of hydrochloric acid into the catalyst regenerator at such a rate as to correct any perceptible divergence of index I from "unfouled reactor" conditions. It is also possible, by means well-established in the art, to incorporate, in addition, an overriding control, actuated by the alkene vent rate, to prevent the addition of hydrochloric acid in such excess that the vent rate increases above a preset value. Thus, even with a varying catalyst solution throughput rate, the acid introduction rate can be controlled between a lower limit signalled by an increase in index I and an upper limit signalled by an increase in alkene vent rate above any desired preset level, with resulting freedom from process upsets and with maintenance of optimal reactor productivity.

It will be recognized that the alkene vent rate is the mathematical product of two factors: (a) the flow rate of the vent gas stream discharged, for example, through conduit 19 and conveniently metered by a volumetric flow meter and (b) the alkene concentration in this stream, determinable by simple chemical analysis (e.g. by analyzing for unsaturates) but preferably by use of a continuous on-line analyzer employing, for example, infra-red spectroscopy which produces an output signal which can be employed in direct process control. Multiplying instruments are well known which can continuously receive a vent gas flow meter output signal and an output signal from an on-line alkene analyzer, multiply the two together, and transmit an output control signal equivalent to the alkene vent rate which sets the upper acid introduction rate control limit.

EXAMPLE

Ethylene was oxidized to acetaldehyde in the apparatus shown schematically in the drawing FIG. 1. The alkene oxidation reactor was operated at approximately 110°C and at a pressure of approximately 11 atmospheres absolute, while the catalyst solution reoxidation reactor was operated at approximately 115°C and approximately 12 atmospheres absolute. The stripping tower was operated at approximately 1.5 atmospheres absolute, and the catalyst regeneration reactor 15 was operated at approximately 160°C and 13 atmospheres absolute. Oxygen separator pressure $P_1$ was maintained at 11.5 atmospheres absolute. The alkene oxidation discharge pressure $P_2$ varied slightly with fouling conditions in the alkene oxidation reactor as will be explained.

The product recovery system, within which the volatile products, including acetaldehyde, withdrawn from the head of the stripping tower were separated into their several components, was so designed that all fixed gases, including unreacted ethylene, were discharged through a flow meter; provision was also made to analyze the discharged vent gas for its ethylene content.

During operation the total inventory of catalyst solution within the system was maintained at a constant level by adding water as required to compensate for losses of water in the product recovery system.

The composition of the catalyst solution entering the alkene oxidation reactor was approximately as follows:

| Component | Concentration |
|---|---|
| Copper moiety | 1100 millimoles/liter |
| Chloride moiety | 1700 millimoles/liter |
| Palladium moiety | 6 millimoles/liter |
| Acetic acid | 10 weight percent |
| Water | Remainder |

Per square foot of cross section of the alkene oxidation reactor, there was introduced into the reactor approximately 3.5 million lb per hour of the catalyst solution along with 11,000 lb per hour of ethylene of approximately 99% purity. Under these conditions the pressure gradient through the alkene oxidation reactor was 6 lb per square inch, as measured by the pressure differential between the oxygen separator and the discharge end of the alkene oxidation reactor when the reactor was known to be free of solid deposits. The vent gas discharge rate was approximately 5,000 standard cubic feet per hour per square foot of reactor cross-section with the vent gas containing approximately 5% ethylene by volume.

Spent (i.e. chemically reduced) catalyst solution recovered from the base of the stripping tower was continuously recycled to the catalyst reoxidation reactor, at essentially the same rate as that at which the fresh catalyst solution was introduced into the alkene oxidation reactor. Of the copper contained in the spent solution entering the reoxidation reactor, approximately 30% was in cuprous form. Per pound of spent solution entering the reoxidation reactor, approximately 0.2 standard cubic foot of air was admixed, to be passed through the reoxidation reactor cocurrently with the catalyst solution for reoxidation of the contained catalyst components, e.g. copper.

From the oxygen separator, fixed gases, largely nitrogen and unconsumed oxygen, were vented, and the reoxidized catalyst solution was withdrawn from the base of the separator, with 99% of this reoxidized solution withdrawn from the separator being returned to the alkene oxidation reactor while the remaining 1% was diverted to the catalyst regeneration system. That portion of the solution which was diverted to the catalyst regeneration system was admixed with approximately 0.1 lb of 39% aqueous hydrochloric acid per lb of diverted catalyst solution. After passage through the catalyst regeneration reactor, the resulting mixture of regenerated catalyst solution and hydrochloric acid was returned to the catalyst reoxidation reactor was shown in the drawing FIG. 1.

After approximately 5 hours of operation as described above, an increase was noted in the alkene oxidation reactor pressure gradient, as measured by the difference between $P_1$ and $P_2$. The vent gas discharge rate had not changed appreciably at this time, but the increase in alkene oxidation reactor pressure gradient, amounting to an increase of approximately 0.5 lb per square inch over the base pressure gradient noted when the reactor was known to be free of solid deposits, indicated that solids deposition was taking place. When this pressure gradient increase was noted, the hydrochloric acid introduction rate into the catalyst regeneration system was increased by approximately 2.5%. This increased rate of hydrochloric acid addition was maintained until, after approximately 1 hour, the alkene oxidation reactor pressure gradient had declined to its normal base value (characteristic of a clean reactor).

After approximately 1 hour of operation with the hydrochloric acid addition being at the increased rate which had been instituted in response to the increase in reactor pressure gradient, a rise in alkene vent rate was noticed, indicating over-treatment with hydrochloric acid. Specifically, although the total vent gas rate did not increase significantly, the ethylene content of the gas rose to approximately 7%. When this increase in vent gas rate was noted, the hydrochloric acid introduction rate was reduced by approximately 2%, and after approximately 1 hour, the ethylene content of the gas declined to its original base value.

Operation was continued in the manner just described, hydrochloric acid introduction rate being increased in response to a rise in alkene oxidation reactor pressure gradient and decreased in response to a rise in vent gas evolution rate, and the apparatus was operated at high chemical efficiency and process throughput over a period of approximately 3 months without experiencing upset conditions. The average acetaldehyde production efficiency obtained was approximately 2% higher than that which had previously been obtained when operating on the basis of periodic chemical analyses of the catalyst solution followed by adjustment of concentrations in accordance with the results of the analyses.

The embodiments of the invention in which an exclusive property or privilege is claimed are defined as follows:

1. In a process which comprises converting an alkene to an oxygenated derivative thereof, which process comprises the step of:

passing said alkene through an elongated tubular reaction zone cocurrently with an acidic oxidant catalyst solution comprising a liquid containing a noble metal oxidation catalyst, cupric ions, and chloride ions;

oxidizing said alkene with said catalyst solution in said reaction zone to form a reaction product comprising predominantly said oxygenated derivative admixed with said catalyst solution in a chemically reduced condition;

separating said reaction product into fractions comprising (a) an oxygenated product fraction and (b) a reduced catalyst solution fraction containing said noble metal and copper in a reduced form;

reoxidizing said reduced catalyst solution with a gas comprising molecular oxygen to oxidize the copper values contained therein to the cupric form; and recycling the resulting reoxidized catalyst solution to said elongated reaction zone for the oxidation of additional quantities of said alkene;

said process being characterized by continuous depletion of the chloride content of said catalyst solution through formation of chlorinated reaction by-products, making necessary the replenishment of the chloride content of said catalyst solution by adding hydrochloric acid thereto prior to said reoxidation step;

the improvement which comprises:

maintaining the catalytic activity of said oxidation catalyst solution at an optimal level by continuously monitoring the internal pressure gradient obtaining within said reactor at a given rate of discharge of said reaction product therefrom and adjusting the rate of addition of said hydrochloric acid into said catalyst solution, in response to fluctuations in said pressure gradient, to such a level as to maintain said pressure gradient substantially constant and at a level characteristic of said reactor when its interior is free of solid foulants.

2. The improvement of claim 1 wherein said adjustment comprises:

a. increasing said rate of hydrochloric acid addition by successive increments, in response to an observed increase in said reactor pressure gradient, from a base rate of hydrochloric acid addition obtaining at the time of said pressure gradient increase, until an elevated rate of hydrochloric acid addition is reached at which a downward trend in said pressure gradient is observed;

b. maintaining said elevated rate of hydrochloric acid addition until said reactor pressure gradient has declined to the level obtaining prior to said observed increase therein;

c. reducing the rate of hydrochloric acid addition again, by successive increments, to an adjusted rate at which a second increase in reactor pressure gradient is observed; and, d. repeating steps (a), (b), and (c) above to maintain an average hydrochloric acid addition rate which is substantially equal to, but greater than, that rate at which a progressive increase in said reactor pressure gradient first becomes perceptible.

3. The improvement of claim 2 wherein said alkene is ethylene, said oxygenated derivative is acetaldehyde, said noble metal is palladium, and said catalyst solution comprises predominantly an aqueous solution of copper chlorides, palladium species including palladous chloride, and hydrochloric acid.

4. The improvement of claim 1 wherein said alkene is ethylene, said oxygenated derivative is acetaldehyde, said noble metal is palladium, and said catalyst solution comprises predominantly an aqueous solution of copper chlorides, palladium species including palladous chloride, and hydrochloric acid.

5. In a process which comprises converting a gaseous alkene to a carbonyl derivative thereof, which process comprises the steps of:
   passing said alkene through an elongated tubular reaction zone cocurrently with an acidic oxidant solution comprising a liquid containing a noble metal oxidation catalyst, cupric ions, and chloride ions;
   oxidizing said alkene with said catalyst solution in said reaction zone to form a reaction product comprising predominantly a mixture of said carbonyl derivative with said catalyst solution in a chemically reduced condition;
   withdrawing said reaction product from said reaction zone and separating said product into (a) a liquid reaction comprising predominantly said carbonyl derivative, (b) a reduced catalyst solution fraction comprising predominantly a reaction solvent containing said noble metal with copper in chemically reduced form, and (c) an alkene vent stream comprising components of said reaction product which are higher in volatility than said carbonyl derivative and containing specifically that fraction of said alkene which has passed through said reaction zone chemically unconverted;
   reoxidizing said reduced catalyst solution fraction with a gas comprising molecular oxygen to oxidize the copper values contained therein to the cupric form; and
   recycling the resulting reoxidized catalyst solution fraction to said reaction zone for use in converting additional quantities of said alkene,
   said process being characterized by continuous depletion of the chloride content of said catalyst solution through formation of chlorinated reaction by-products which necessitates replenishment of the chloride content of said catalyst solution by adding hydrochloric acid thereto prior to said reoxidation step,
   the improvement which comprises maintaining the catalytic activity of said oxidant catalyst solution at an optimal level by:
   continuously monitoring the rate of production of said vent stream, the alkene content of said vent stream, and the pressure gradient obtaining within said reactor at a given rate of alkene and catalyst solution throughput therethrough, and
   controlling said hydrochloric acid addition rate, in response to variations in the rate of discharge of alkene in said vent stream and said reactor pressure gradient, between an upper limit signalled by the inception of a rising trend in said rate of alkene discharge and a lower limit signalled by the inception of an upward trend in said reactor pressure gradient.

6. The process improvement of claim 5 wherein said alkene is ethylene, said carbonyl derivative is acetaldehyde, said noble metal is palladium, and said catalyst solution comprises predominantly water.

7. The improvement of claim 6 wherein the method of controlling the hydrochloric acid addition rate comprises:
   observing, at a given catalyst solution throughput rate and with an ethylene throughput rate substantially equal to that rate at which a set finite concentration of ethylene first appears in said vent stream as determinable by chemical analysis thereof, the lowest reactor pressure gradient obtainable by incrementally adjusting the hydrochloric acid addition rate and observing the resulting trend in reactor pressure gradient until a base acid addition rate is attained at which further increases therein do not result in further perceptible pressure gradient decreases while further decreases therein result in pressure gradient increases;
   setting said lowest reactor pressure gradient as a first process output for control purposes;
   with hydrochloric acid being continuously added at said base rate, observing the flow rate of said vent stream while ethylene is being passed through said reactor at such a rate that unreacted ethylene appears in said vent stream in a set desired concentration as determinable by analysis of said vent stream;
   setting as a second process output for control purposes an alkene vent rate, which is the product of said flow rate of said vent stream and said set desired concentration of alkene therein; and thereafter
   continuously adjusting said base acid addition rate as required, in response to said first and second process outputs, between an upper level at which alkene vent rate begins to increase and a lower level at which said reactor pressure gradient begins to increase.

8. The improvement of claim 6 wherein the rate of flow of said catalyst solution through said reactor is subject to deviations from time to time from a desired set constant rate and wherein said lower limit of hydrochloric acid addition rate is controlled in response to a solution flow rate-compensated reactor pressure gradient, said control comprising adding hydrochloric acid in an amount sufficient to maintain $\Delta M$ at zero in the equation:

$$\Delta M = C_1 [\Delta(P_1-P_2)-C_2\Delta F_R)]$$

wherein $M$ is the reactor pressure gradient compensated for deviation in catalyst solution throughput, $(P_1-P_2)$ is the reactor pressure gradient as actually measured, $F_R$ is the rate of solution throughput through the reactor, $C_1$ and $C_2$ are positive constants, and the notation $\Delta$ signifies a change in the indicated term.

9. The improvement of claim 8 wherein the rate of hydrochloric acid addition is controlled by flow control means sensing the output signals of (a) transmitting flow rate-sensing means sensing an indication of the rate of flow of said vent stream and of the ethylene content thereof, (b) transmitting pressure-sensing means sensing an indication of the pressure differential between the intake and discharge ends of said reactor, and (c) transmitting flow-sensing means sensing an indication of the rate of discharge of reaction product from said reactor.

10. The improvement of claim 9 wherein said reaction product is discharged from said reactor through a throttle valve operating at a substantially constant discharge pressure lower than that obtaining within the reactor, and wherein said indication of the rate of discharge of reaction product from said reactor comprises (a) an indication of the degree to which said valve is open from its closed position and (b) an indication of the pressure drop across said valve.

* * * * *